(12) United States Patent
Park

(10) Patent No.: US 8,282,541 B2
(45) Date of Patent: Oct. 9, 2012

(54) DEVICE FOR STERILIZING VIRUS OR BACTERIA BY USING RADIOISOTOPE GAS

(76) Inventor: Young-Woong Park, Daejeon (KR)

( * ) Notice: Subject to any disclaimer, the term of this patent is extended or adjusted under 35 U.S.C. 154(b) by 1448 days.

(21) Appl. No.: 11/766,512

(22) Filed: Jun. 21, 2007

(65) Prior Publication Data

US 2008/0108858 A1     May 8, 2008

Related U.S. Application Data

(63) Continuation-in-part of application No. PCT/KR2005/004407, filed on Dec. 21, 2005.

(30) Foreign Application Priority Data

Dec. 21, 2004 (KR) .......................... 10-2004-0109105
Feb. 1, 2005 (KR) .......................... 10-2005-0008908

(51) Int. Cl.
*A61N 5/00* (2006.01)
*A61M 36/00* (2006.01)
(52) U.S. Cl. ........................................................ 600/1
(58) Field of Classification Search ................ 600/1–8; 424/1.11–1.89; 423/1–20, 249–261
See application file for complete search history.

(56) References Cited

U.S. PATENT DOCUMENTS
6,454,695 B1 * 9/2002 Morishige .......................... 600/1

FOREIGN PATENT DOCUMENTS

| JP | 57016814 A | * | 1/1982 |
| KR | 1020050007244 A | | 1/2005 |
| KR | 1020050032047 A | | 4/2005 |
| RU | 2066548 C1 | * | 9/1996 |

OTHER PUBLICATIONS

Shliapak EA, Gabidova NT, Evseeva SN, Apanasevich ZK, Shvedunova LN. A low-frequency alternating magnetic field and its combination with radon baths in juvenile rheumatoid arthritis. Vopr Kurortol Fizioter Lech Fiz Kult. Jul.-Aug. 1992; (4): 13-7.*
English Abstract corresponding to KR 1020050007244 A, Jan. 17, 2005.
English Abstract corresponding to KR 1020050032047 A, Apr. 6, 2005.
Park, Y.W., "Curing the AIDS by using the Gaseous Radioisotopes," published at http://old.Rn-tech.com>Reference Room, No. 94, Jun. 25, 2007, 7 pgs.

* cited by examiner

*Primary Examiner* — Charles A Marmor, II
*Assistant Examiner* — Catherine E Burk
(74) *Attorney, Agent, or Firm* — Brooks Kushman P.C.

(57) ABSTRACT

An apparatus for sterilizing a blood vessel in a patient's inner skin includes a generator for providing gaseous radioisotope and a chamber adapted to exposure of a portion of a patient's body to the gaseous radioisotopes. When a patient is contacted with gaseous radioisotopes, alpha and beta particles are emitted from the gaseous radioisotopes into inner skin of the patient. Ultraviolet rays, subsequently emitted from the skin, sterilize viruses or bacteria present in a blood vessel. A method of treating a patient with the apparatus is also provided.

3 Claims, 3 Drawing Sheets

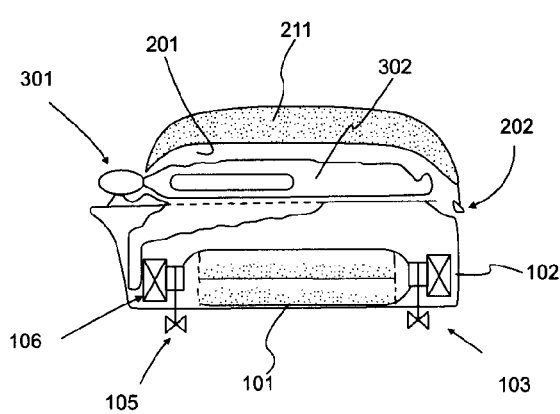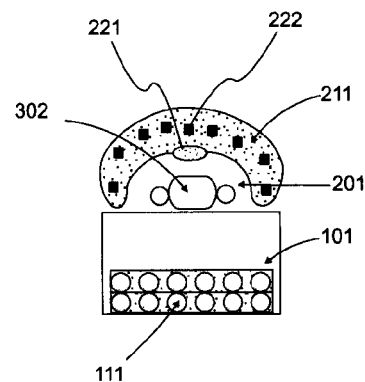
Fig. 5A        Fig. 5B
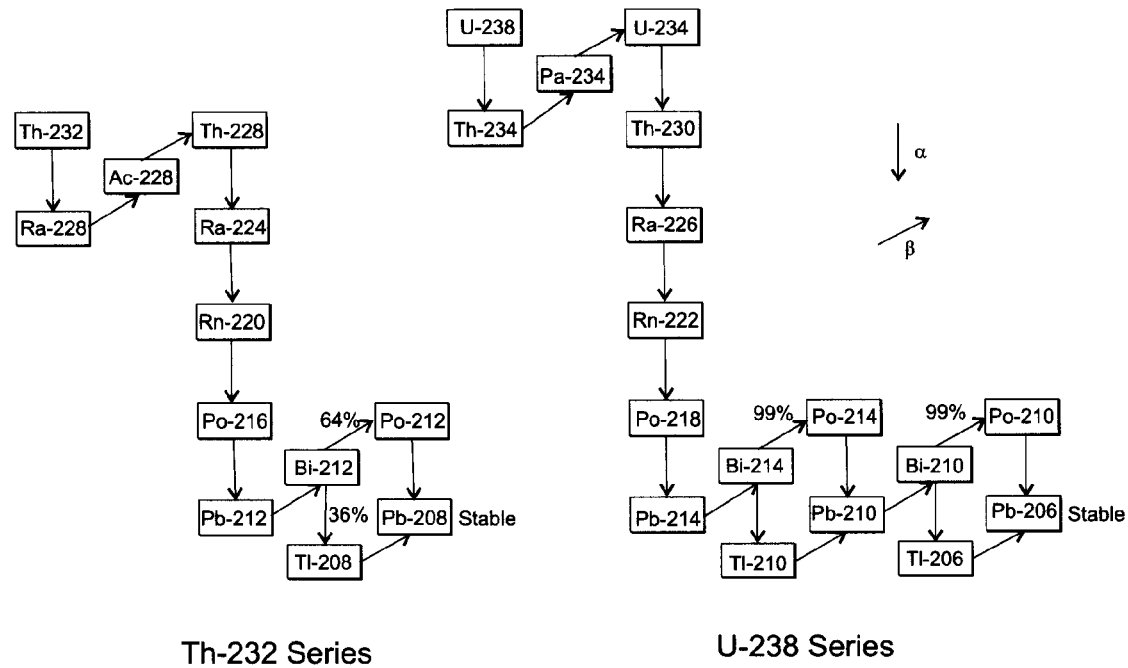
Th-232 Series        U-238 Series
Fig. 6

US 8,282,541 B2

DEVICE FOR STERILIZING VIRUS OR BACTERIA BY USING RADIOISOTOPE GAS

CROSS-REFERENCE TO RELATED APPLICATIONS

This application is a continuation-in-part of PCT/KR2005/004407 filed Dec. 21, 2005, published in English, claiming the benefit of Korean patent application 10-2004-0109105 filed Dec. 21, 2004 and of Korean patent application 10-2005-0008908 filed Feb. 1, 2005. These applications are hereby incorporated by reference in their entirety.

BACKGROUND OF THE INVENTION

1. Field of the Invention

The present invention relates to methods for sterilizing viruses or bacteria existing in the blood vessel with the cell of inner skin.

2. Background Art

Acquired Immune Deficiency Syndrome ("AIDS") is caused by the HIV virus is transmitted by sexual relations, blood transfusion, or inter-venous drug. It is called the 21st century's plague because an effective cure has not been developed even though the disease was first described in 1981.

Since the HIV virus's genetic information is encoded within RNA, reproduction of the HIV is not possible without using the reproduction function of a living subject. Specially, during reproduction HIV use CD-4 cell, which is a type of leukocyte. Loss of immunity occurs after destruction of infected CD-4 cells.

Heretofore, efforts for minimizing AIDS include education, vaccine developments, and the development of various treatment protocols. Among these efforts, some treatment protocols prevent HIV from forming DNA from its native RNA or preventing HIV from multiplying in the CD-4 cells. In additional protocols, various medicines are used to treat secondary infections by other microbe. In spite of these efforts, complete recovery from AIDS is complicated by occurrence of the variations of the HIV virus.

In addition to treatment by various drugs, exposure to ultraviolet rays from an UV-lamp is used to treat the swelling on the skin that occurs in a late stage of AIDS. However, complete treatment of this condition is not possible because energy from the ultraviolet rays cannot reach into the blood vessel.

Accordingly, there is a need for improved methods for sterilizing blood vessels with minimal deleterious effects.

SUMMARY OF THE INVENTION

The present invention solves one or more problems of the prior art by providing in at least one embodiment, an apparatus for sterilizing a blood vessel in a patient's inner skin. Characteristically, the blood vessel contains viruses and/or bacteria. The apparatus of this embodiment includes a generator for providing gaseous radioisotope and a chamber adapted to exposure of a portion of a patient's body to the gaseous radioisotopes. When a patient is contacted with gaseous radioisotopes, alpha and beta particles are emitted from the gaseous radioisotopes into inner skin of the patient. Ultraviolet rays, subsequently emitted from the skin, sterilize viruses or bacteria present in a blood vessel.

In another embodiment of the invention, a method of sterilizing a blood vessel in a patient's inner skin is provided. The method of this embodiment comprises contacting a portion of a patient's body with a gaseous radioisotopes such that ultraviolet rays are emitted into the blood vessel, the ultraviolet rays sterilizing the viruses or bacteria present in the blood vessel.

BRIEF DESCRIPTION OF THE DRAWINGS

FIG. 5 is an illustration of a device showing horizontal and longitudinal section drawing; and FIG. 6 is an illustration showing the decay series of U-238 and Th-232.

DETAILED DESCRIPTION OF THE PREFERRED EMBODIMENT(S)

Figure 1:
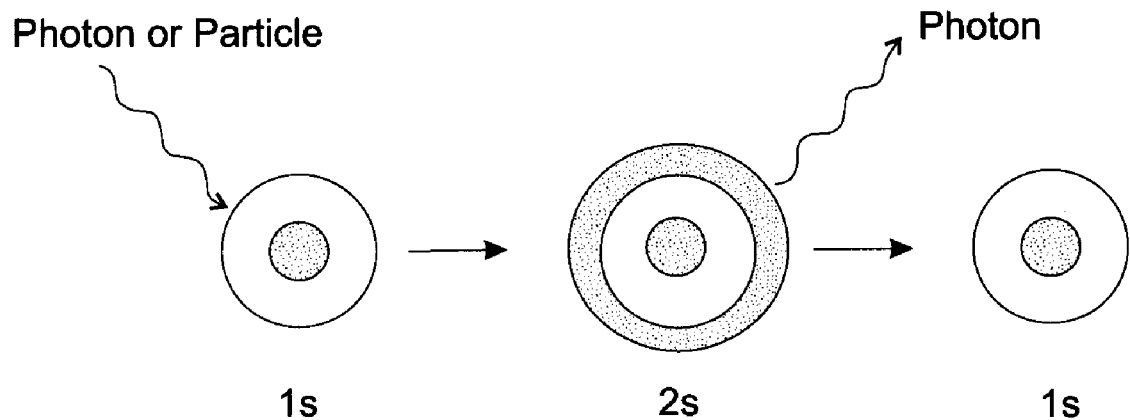
FIG. 1 is an illustration showing an electromagnetic wave from a hydrogen atom soon after collision with the alpha or beta particles.
Figure 2:
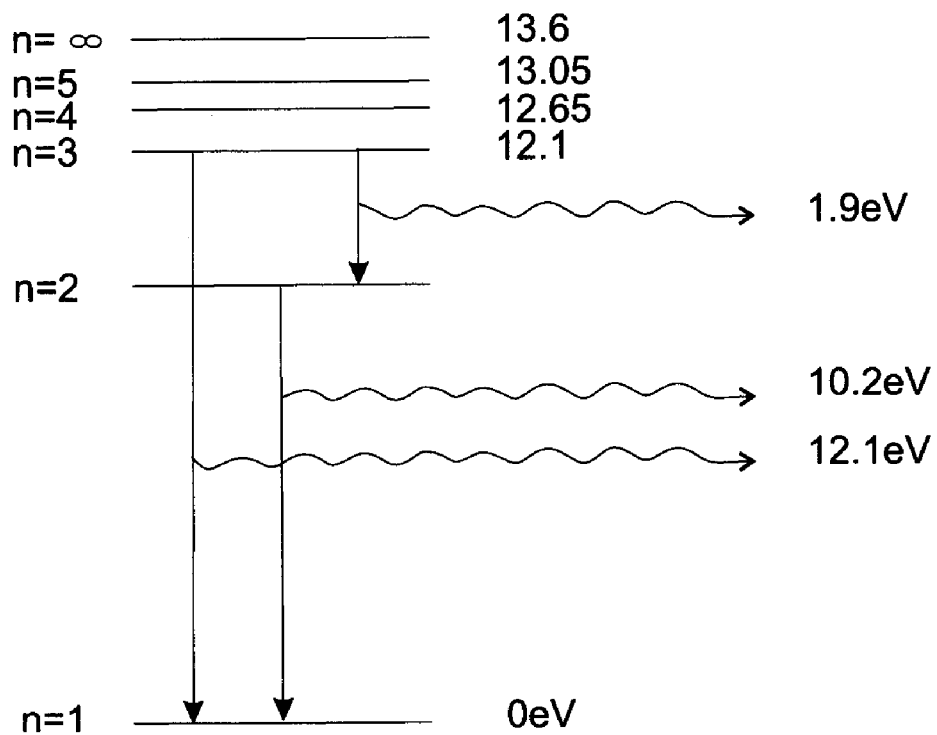
FIG. 2 is an illustration showing that the energy of the electromagnetic wave emitted from the excited hydrogen atom.
Figure 3:
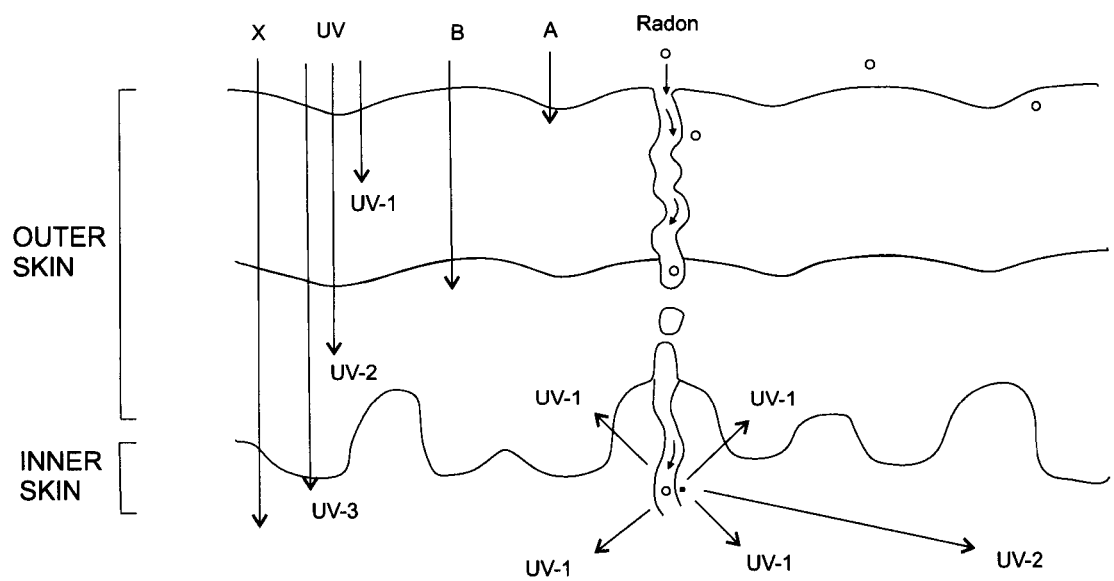
FIG. 3 is an illustration of various penetrations of electromagnetic wave into skin, alpha particle (A), beta particle (B), ultraviolet rays (UV-1, UV-2, UV-3), and X-ray (X), and the UV-I and UV-2 to the blood vessel after diffusion of the radioisotope gases (Rn-222, Rn-220, Rn-219) to the inner skin through a sweat pore.
Figure 4:
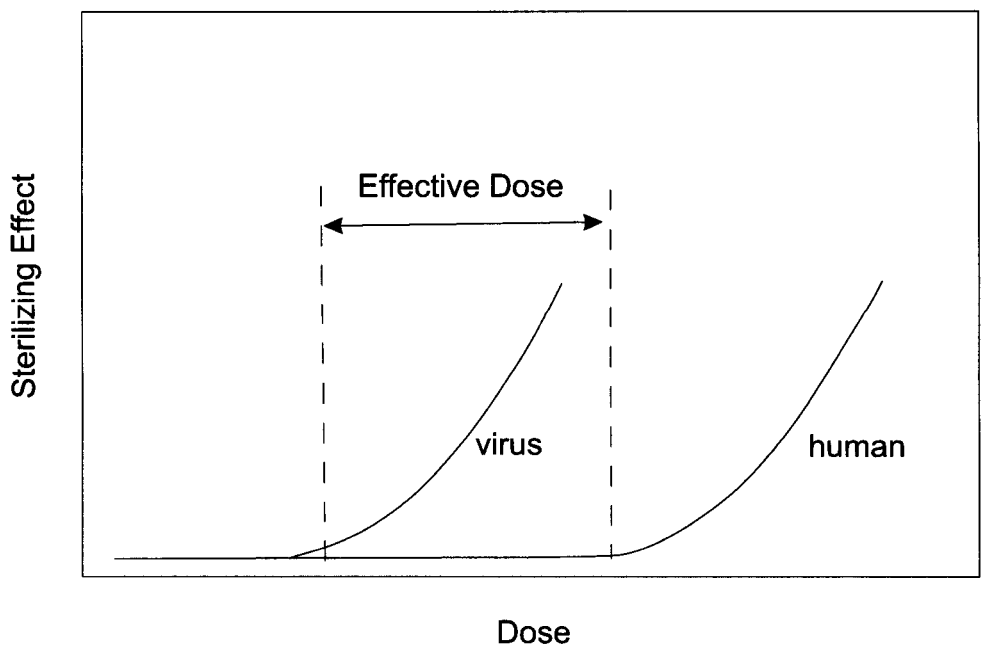
FIG. 4 is an illustration showing an effective dose to sterilize virus or bacteria without side effects to the human body.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. The description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application in their entirety to more fully describe the state of the art to which this invention pertains.

Generally, virus and bacteria are sterilized by exposure to heat or electromagnetic radiation. Although inanimate objects such as the syringe are sterilized by gamma rays or X-rays, living subjects cannot be so treated because of the deleterious side effects to living tissues. However, it is known that viruses and bacteria can be sterilized without side effects to the living subject by using ultraviolet rays if such rays are able to reach a targeted blood vessel containing the virus or the bacteria with the cell of inner skin are sterilized beneath a harmful dose to the human.

TABLE 1

Do-values of cell nucleus for various systems.

| Cell nucleus | | Do-value | |
|---|---|---|---|
| Name | Species | Do(UV), J/m$^2$ | Do(X-ray), Gy |
| T$_1$-phage | Virus | 41 | 2,600 |
| E. coli B/r | Bact. | 85 | 30 |
| Bacillus subtilis | Bact. | 50 | 33 |
| Saccharomyces | Yeast | 1,150 | 150 |
| Chlamydomonas | Alga | 2,500 | 24 |
| Hamster cells | Mammal | 50 | 1.4 |
| HeLa cells | Human | 108 | 1.4 |

Do: Relative survival dose to 37% of surviving fraction, which can be sensitivity to electromagnetic waves.

Electromagnetic waves are classified by energy. Visible light has an energy from 1.61 eV to 3.18 eV. Ultraviolet light has an energy from 3.18 eV to 1.24 KeV. X-rays are characterized as having energies from about 1.24 keV to 248 keV. Finally, gamma rays are characterized as having energies greater than X-rays.

Gamma rays and the X-rays are more harmful than the low energy of ultraviolet rays. The increase deleterious effect of gamma and X-rays is the result of the energies of these rays being higher than the ionization energy of hydrogen (13.6 eV) and carbon (11.27 eV) which are the principal elements of the human body.

With reference to Table 1, the 37% survival dose to virus, bacteria, and human by ultraviolet rays are 35 J/m$^2$, 50 J/m$^2$, and 103 J/m$^2$ respectively. The permissible dose to the human by ultraviolet rays is 60 J/(m$^2$·day). Accordingly, a dose of 60 J/(m$^2$·day) by ultraviolet rays could bring down the virus and the bacteria without side effects to the human body.

Direct methods using a UV-lamp are not suitable for treating patients because the penetrating power of ultraviolet rays is less than X-rays or gamma rays. Moreover, an excessive dose of ultraviolet rays may also cause skin cancer. Accordingly, the utilization of indirect ultraviolet irradiation using the methods and apparatuses of the present invention is particularly useful.

In an embodiment of the present invention, a method for sterilizing viruses and bacteria is provided. In accordance with the method of this embodiment, a blood vessel containing viruses and/or bacteria is sterilized by indirect exposure using a radioisotope gas that emits alpha particles. Radon gas (Rn-222) and its radioisotopes (Rn-220, Rn-219) are readily absorbed reaching the inner skin via sweat pores and skin wrinkles. Alpha and beta particles are emitted from the decay series of U-238, Th-232, and U-235. (Rn-222→Po-218→Pb-214→Bi-214→Po-214→Pb-210→Bi-210→Po-210→Pb-206, Rn-220→Po-216→Pb-212→Bi-212→Po-212→Pb-208, Rn-219→Po-215→Pb-211→Bi-211→Tl-207→Pb-207). The ultraviolet rays from the interaction of the alpha and beta particles with the inner skin molecules sterilize the virus or the bacteria existing in the blood vessel.

HIV can be sterilized in a few minutes by exposure to ultraviolet rays from tens to hundreds J/m$^2$ when an irradiated region is also heated to a temperature from about 70 to 80° C. The treatment efficiency of the present embodiment using radioisotope gas is enhanced by heating the surface of the skin from 20° C. to 60° C. Moreover, application of a magnetic field from 100 to 100,000 gauss shift the energy of the applied ultraviolet rays to a more suitable energy for sterilizing virus or bacteria.

In a variation of the present embodiment, the radioisotope gas diffuses to the inner skin via sweat pores and skin wrinkles. The radioisotope gas emits alpha and beta particles in the inner skin such that the energy of inner skin molecules is excited by the interaction with the alpha and beta particles. Ultraviolet rays are emitted from the excited skin molecules by the energy balance upon transitioning to the ground state energy. The thus formed ultraviolet rays sterilize the virus or the bacteria. In a refinement, the ultra violate rays derived from this indirect exposure method sterilize the viruses or the bacteria existing in blood vessels within the inner skin.

TABLE 2

Wavelengths of electromagnetic waves from excited skin molecules and decay series elements.

| From skin molecules | | From radon and its daughters | |
|---|---|---|---|
| Elements | Wavelength (nm) | Elements | Wavelength (nm) |
| C—H | 340 | Rn | 115 |
| N—H | 318 | Po | 147 |
| O—H | 270 | Pb | 167 |
| H$_2$O | 124 | Bi | 170 |

Wavelength(nm) = 1,240/E(eV)

The indirect exposure method of the present invention is advantageously used to sterilize viruses or the bacteria present in blood vessels within cells of the inner skin. In addition to being useful for treating AIDS, the methods of the invention may also be used for treating additional viruses or and bacteria, examples of which include, but are not limited to, smallpox, leprosy, varicella, eczema, bacterial arthritis, and viral leukemia.

The methods of the present invention provide adequate medical efficiency when the dosage is sufficient to sterilize the viruses or bacteria in the blood vessel. Moreover, in order to be effective, the patient must be safe during treatment. Particularly useful radioisotope gases emitting alpha rays include Rn-222, Rn-220, and Rn-219. In a variation of the invention, thoron (Rn-220) is more useful than radon (Rn-222), because thoron (Rn-220, T$_{1/2}$: 55.6 seconds) is less harmful than radon (Rn-222, T$_{1/2}$: 3.82 days).

TABLE 3

Types of natural ore which included thorium (Th-232) and contents of thorium included in the ore.

| | Chemical forms | Contents of ThO2 (%) |
|---|---|---|
| Monazite | (Ce,La,Nd,Th)PO4 | 5~10 |
| Thorite | ThSiO4 | 49~74 |
| Thorianite | (ThU)O2 | 59~93 |
| Brannerite | (U,Ca,Ce)(Ti,Fe)2O6 | 47.5 |
| Cerianite | (Ce,Th)O2 | 4.5 |
| Loparite | (Ce,Th,Na,Ca)2(Ti,Nb)2O6 | 11.5 |
| Polymignite | (Ca,Fe,Y,Th)(Nb,Ti,Ta,Zr)O4 | 3.5 |
| Britholite | (Ca,Ce)5(SiO4PO4)3(OH,F) | 17 |
| Grayite | (Th,Pb,Ca,Ce)PO4(H2O) | 37 |
| Huttonite | ThSiO4 | 71.5 |

With reference to FIGS. 5A and 5B, a schematic illustration of an apparatus implementing a variation of the present invention is provided. In order to prevent inhalation of the radioisotope gases during treatment and to realize the effective dose to the patient or infected person, the apparatus is divided into the generator 101 and the chamber 201. Generator 101 is filled with source materials that generate the radioisotope gases (Rn-222, Rn-220, and Rn-219). Chamber 201 includes cover 211 and is typically air-tight. Chamber 201 is surrounded by heaters 221 and magnets 222.

In order to flow the radioisotope gas easily to the chamber 201, generator 101 is composed of pipes 111 that are filled with a powdered ore. In a variation, there are between about 1 to about 1,000 pipes that are filled from about 1% to about 99% the powdered ore. The total weight of radioactive materials in generator 101 is sufficient to provide a curative effect. When thoron (Rn-220) is used, generator 101 is filled with the powder of ore between about 10 g to about 1,000 kg based on the $ThO_2$. When radon (Rn-222) is used, a chemical compound of radium can be used in addition to or instead of the powdered ore. When a chemical compound is used, generator (101) is filled with the compound of radium (Ra-226) in a amount from about 10 mg to about 10 kg base on the radium.

In another embodiment of the present invention, a method for sterilizing viruses and bacteria in an apparatus is provided. With reference to FIGS. 5A and 5B, the method of this embodiment provides an operating procedure of the device to realize this invention is as follows. A patient lies down with body 302 inside of chamber 201. Cover 211 is closed. A hose with a pump is connected to the outlet 202 of the chamber 201. Valves 103, 105 are then opened. The pump is operated with the flow rate of the resulting flow stream being regulated. The flow stream is directed to the inside of chamber 210 through pre-filter 102 and dust collection filter 106 with the radioisotope gases (Rn-222, Rn-220, Rn-219) from generator 101. Valves 103, 105 are closed at the end of the exposure to the radioisotope gases. After 10 minutes (a time sufficient for the substantially extinction of the radioactivity of thoron (Rn-220)), the pump is operated to discharge radioactive gas in chamber 201. Finally, cover 211 is opened to allow a patient to exit the apparatus.

The medical efficiency of various embodiments of the present invention is based on the "hot spring cure." In this method, the hot spring is loaded with various isotopes of radon is thought to have a curing efficiency for chronic arthritis, rheumatism, ventilation, and the like. The medical effectiveness of the present invention is optimally realized when the treatment is repeated over several weeks or several months.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An apparatus for sterilizing a blood vessel in a patient's inner skin, the blood vessel containing viruses and/or bacteria, the apparatus comprising:
    a generator of thoron (Rn-220), the generator comprising powdered ore having $ThO_2$ in an amount from 10 grams to 1,000 kilograms;
    a chamber for exposing a portion of a patient's body to the thoron including a cover to avoid contacting a patient's head with the thoron; and
    the generator and the chamber being connected by piping with a valve.

2. The apparatus of claim 1 wherein the chamber further comprises a heater to control temperature of a patient's skin between 20 to 60° C. during treatment.

3. The apparatus of claim 1 wherein the chamber further comprises magnets that provide a magnetic field surrounding the patient having a strength between about 100 to about 100,000 gauss during treatment.

* * * * *